United States Patent
Fritsch et al.

(10) Patent No.: US 11,911,195 B2
(45) Date of Patent: Feb. 27, 2024

(54) VISUAL INDICATOR SYSTEM FOR PATIENT BED

(71) Applicant: Siemens Medical Solutions USA, Inc., Malvern, PA (US)

(72) Inventors: Benjamin Fritsch, Elgin, IL (US); Ansgar Graw, Chicago, IL (US); Michael Zochowski, Buffalo Grove, IL (US); Evan Qi, Lone Tree, CO (US); William Danziger, La Grange Park, IL (US); Benedict Donahue, Lexington, MA (US); Patanit Sanpitak, Highland Park, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 855 days.

(21) Appl. No.: 15/733,551

(22) PCT Filed: May 10, 2018

(86) PCT No.: PCT/US2018/031986
§ 371 (c)(1),
(2) Date: Aug. 26, 2020

(87) PCT Pub. No.: WO2019/216896
PCT Pub. Date: Nov. 14, 2019

(65) Prior Publication Data
US 2020/0397390 A1    Dec. 24, 2020

(51) Int. Cl.
*A61B 6/04* (2006.01)
*G16H 40/63* (2018.01)
(Continued)

(52) U.S. Cl.
CPC .......... *A61B 6/0492* (2013.01); *A61B 6/0407* (2013.01); *F21V 33/0072* (2013.01);
(Continued)

(58) Field of Classification Search
CPC ....... A61B 6/0492; A61B 6/465; A61B 6/469; A61B 6/0407; A61B 6/037; A61B 5/055;
(Continued)

(56) References Cited

U.S. PATENT DOCUMENTS

| 54,272 A | 5/1866 | Adams |
| 5,452,721 A | 9/1995 | Hacker |

(Continued)

FOREIGN PATENT DOCUMENTS

| CN | 103445865 A | 12/2013 |
| CN | 105615908 A | 6/2016 |

(Continued)

OTHER PUBLICATIONS

International Search Report dated Jan. 16, 2019 in corresponding PCT Application No. PCT/US2018/031986.

*Primary Examiner* — Irakli Kiknadze

(57) ABSTRACT

Embodiments can provide a visual indicator system, attachable to a medical imaging patient bed. The visual indicator system comprising: one or more light strips, each light strip comprising a plurality of lights; a distance meter, attachable to one end of the medical imaging patient bed; a storage device, configured to store one or more preconfigured finger gestures; and a microcontroller. The one or more light strips are attachable to the medical imaging patient bed; wherein the microcontroller is configured to illuminate the one or more light strips after the one or more preconfigured finger gestures are made with respect to the one or more light strips. A position of the illumination of the light strip corresponds to a position of performing the one or more preconfigured finger gestures and one or more distance measurements received from the distance meter.

29 Claims, 19 Drawing Sheets

(51) Int. Cl.
*G05B 19/4155* (2006.01)
*G08B 5/36* (2006.01)
*A61B 6/03* (2006.01)
*A61B 6/00* (2006.01)
*F21V 33/00* (2006.01)
*G01S 17/08* (2006.01)
*G01G 19/52* (2006.01)
*G01S 15/08* (2006.01)

(52) U.S. Cl.
CPC .......... *G01S 17/08* (2013.01); *G05B 19/4155* (2013.01); *G08B 5/36* (2013.01); *G16H 40/63* (2018.01); *A61B 6/032* (2013.01); *A61B 6/037* (2013.01); *A61B 6/582* (2013.01); *G01G 19/52* (2013.01); *G01S 15/08* (2013.01); *G05B 2219/35444* (2013.01)

(58) Field of Classification Search
CPC ....... A61B 6/582; A61B 6/032; A61B 5/7475; A61B 6/0487; A61B 6/467; A61B 6/545; A61B 6/547; A61B 2090/061; A61B 6/04; A61B 6/08; A61B 6/56; A61B 6/4464; A61B 6/40; A61B 6/4452; A61B 6/544; A61B 6/42; A61B 6/4476; A61B 6/5205; A61B 6/463; A61B 6/548; A61B 6/487; A61B 6/5235; A61B 6/5241; A61B 6/03; A61B 5/743; A61B 5/7275; A61B 5/1077; A61B 5/015; A61B 5/1079; A61B 5/444; A61B 5/445; A61B 5/1075; A61B 5/0071; A61B 5/1072; A61B 6/461; A61B 6/488; A61B 6/505; A61B 5/0064; A61B 5/0077; A61B 5/70; A61B 5/7425; A61B 8/4245; A61B 8/40; A61B 5/06; A61B 5/702; A61B 5/1114; A61B 6/00; G08B 5/36; G01S 17/08; G01S 15/08; G05B 19/4155; G05B 2219/35444; F21V 33/0072; G16H 40/63; G01G 19/52; G01B 11/02; G01B 17/00; G01B 11/14; A61G 7/05; G06T 7/11; G06T 7/37; G06T 7/75; G06T 2207/10028; G06T 2207/30004; G06T 7/0012; G06V 40/103; G06V 2201/12; G06V 2201/03; G01L 5/00
USPC .......................................................... 378/20
See application file for complete search history.

(56) References Cited

U.S. PATENT DOCUMENTS

| | | | |
|---|---|---|---|
| 6,208,250 | B1 | 3/2001 | Dixon et al. |
| 9,610,476 | B1 | 4/2017 | Tran et al. |
| 11,490,782 | B2* | 11/2022 | Rafii-Tari ............... A61B 34/35 |
| 2006/0034421 | A1 | 2/2006 | Barkow et al. |
| 2008/0261255 | A1 | 10/2008 | Tolosa et al. |
| 2009/0033917 | A1 | 2/2009 | Bak et al. |
| 2009/0285357 | A1 | 11/2009 | Khamene et al. |
| 2012/0317724 | A1 | 12/2012 | Buettner et al. |
| 2013/0345543 | A1* | 12/2013 | Steibel, Jr. ............ A61M 21/02 |
| | | | 600/407 |
| 2013/0345718 | A1* | 12/2013 | Crawford ........... A61B 17/8866 |
| | | | 606/130 |
| 2014/0185107 | A1 | 7/2014 | Li et al. |
| 2015/0363002 | A1 | 12/2015 | Fuhrmann et al. |
| 2016/0370870 | A1 | 12/2016 | Hengerer et al. |
| 2017/0071573 | A1 | 3/2017 | Takahashi |
| 2017/0112416 | A1 | 4/2017 | Hao et al. |
| 2017/0143292 | A1 | 5/2017 | Yun et al. |
| 2017/0143429 | A1* | 5/2017 | Richmond ............. A61B 34/37 |
| 2017/0228104 | A1* | 8/2017 | Ziraknejad ............ A61B 90/37 |

FOREIGN PATENT DOCUMENTS

| | | |
|---|---|---|
| CN | 106922190 A | 7/2017 |
| DE | 202014008084 U1 | 11/2014 |
| DE | 102014216718 A1 | 2/2016 |
| DE | 102014218558 A1 | 6/2023 |
| WO | 2016026758 A1 | 2/2016 |
| WO | 2019078884 A1 | 4/2019 |

* cited by examiner

| Finger Gesture | Command |
|---|---|
| Swipe | Switch to Scan range planning mode |
| Single tap | Select any position of a scan range |
| Hold & Drag | Move the scan range |
| Double tap | Reset |

FIG. 5

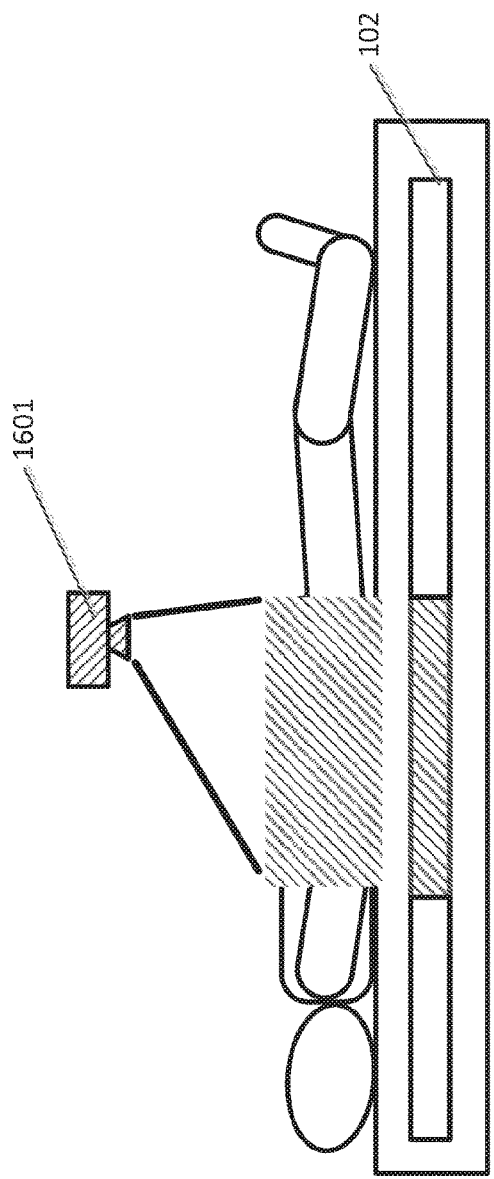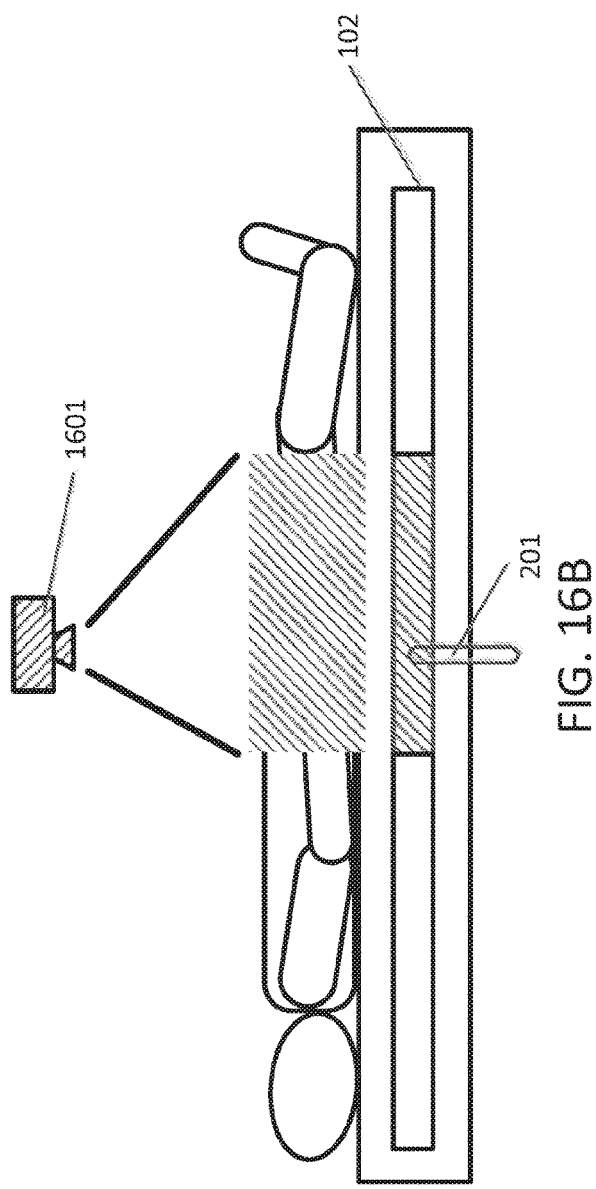

VISUAL INDICATOR SYSTEM FOR PATIENT BED

TECHNOLOGY FIELD

The present invention relates generally to a visual indicator system for a patient bed. This may be applied, for example, to allow a health care provider or other clinic user to easily plan a scan range on a patient bed, alert the clinic user to the status of medical imaging session, and provide interactive aesthetic animations to relieve anxiety of patients.

BACKGROUND

Current imaging patient beds lack the ability to show and adjust the relevant details of a scan range prior to an imaging acquisition (especially in the case of whole body imaging). Due to the lack of direct visual correlation between the scan range and actual patients, the scan range may be incorrect. If the scan range is larger than necessary, this could result in wasted scan time. Conversely, if the scan range is smaller than necessary, additional scans may be required to provide adequate coverage of the area of interest.

Further, currently there are no attention grabbing solutions that alert the clinical user to the status of the medical imaging session when the clinical user is observing the scan progress from outside the imaging room. This lack of communication may make the clinical user unaware of the progress of the scan, or an error condition due to which the medical imaging system is temporarily paused.

Moreover, conventional imaging patient beds lack calming visualizations for relieving anxiety of patients, especially pediatric patients.

SUMMARY

Embodiments of the present invention address and overcome one or more of the above shortcomings and drawbacks, by providing methods, systems, and apparatuses related to a visual indicator system for a patient bed.

Embodiments can provide a visual indicator system, attachable to a medical imaging patient bed, the visual indicator system comprising: one or more light strips, each light strip comprising a plurality of lights; a distance meter, attachable to one end of the medical imaging patient bed; a storage device, configured to store one or more preconfigured finger gestures; and a microcontroller. The one or more light strips are attachable to the medical imaging patient bed; wherein the microcontroller is configured to illuminate the one or more light strips after the one or more preconfigured finger gestures are made with respect to the one or more light strips. A position of the illumination of the light strip corresponds to a position of performing the one or more preconfigured finger gestures and one or more distance measurements received from the distance meter.

Embodiments can provide a visual indicator system, wherein the microcontroller is further configured to illuminate at least two lights corresponding to a scan range selected through the one or more preconfigured finger gestures. An upper limit of the scan range corresponds to a first light and a lower limit of the scan range corresponds to a second light.

Embodiments can provide a visual indicator system, wherein the microcontroller is further configured to illuminate at least two lights different than previously illuminated lights, corresponding to a first preconfigured finger gesture of moving the scan range, wherein the upper limit of the scan range corresponds to a third light and the lower limit of the scan range corresponds to a fourth light.

Embodiments can provide a visual indicator system, wherein the microcontroller is further configured to illuminate at least two lights different than previously illuminated lights, corresponding to a second preconfigured finger gesture of extending the scan range. The upper limit of the scan range corresponds to a third light while the lower limit of the scan range corresponds to the second light, or the upper limit of the scan range corresponds to the first light while the lower limit of the scan range corresponds to a fourth light.

Embodiments can provide a visual indicator system, wherein the microcontroller is further configured to illuminate additional lights, corresponding to a third preconfigured finger gesture of adding a new scan range. The additional lights correspond to an upper limit of the new scan range and a lower limit of the new scan range.

Embodiments can provide a visual indicator system, wherein the microcontroller is further configured to change one or more of color, saturation, and brightness of the at least two lights, corresponding to a fourth preconfigured finger gesture of adjusting an image quality.

Embodiments can provide a visual indicator system, wherein the microcontroller is further configured to divide the scan range into a plurality of sections, and visualize the plurality of sections on the one or more light strips, corresponding to a fifth preconfigured finger gesture of dividing the scan range. The microcontroller is further configured to visualize a boundary between every two sections on the one or more light strips.

Embodiments can provide a visual indicator system, wherein the visual indicator system further includes an overhead laser or an overhead light mounted above the medical imaging patient bed. The microcontroller is further configured to control the overhead laser or the overhead light to illuminate a part of a human body on the medical imaging patient bed, corresponding to the scan range.

Embodiments can provide a visual indicator system, wherein the microcontroller is further configured to illuminate the one or more light strips when a status of the medical imaging system changes.

Embodiments can provide a visual indicator system, wherein the microcontroller is further configured to illuminate the one or more light strips to form one or more interactive visual animations.

Embodiments can provide a visual indicator system, wherein the microcontroller is further configured to illuminate the one or more light strips to form one or more interactive visual animations.

Embodiments can provide a visual indicator system, wherein the distance meter comprises at least one of a laser distance meter, an ultrasound distance meter, or an infrared distance meter.

Embodiments can provide a visual indicator system, wherein the laser distance meter further comprises: a laser source configured to emit an emitted laser; and a laser receiver configured to receive a reflected laser. The visual indicator system further comprises a reflective portion, attachable to the other end of the medical imaging patient bed and configured to reflect the emitted laser and produce the reflected laser.

Embodiments can provide a visual indicator system, wherein the storage device further includes one or more previous acquisition results, and wherein the microcontroller is further configured to visualize radioactive concentration of the one or more previous acquisition results on the one or more light strips, corresponding to a sixth preconfigured finger gesture of visualizing the radioactive concentration.

Embodiments can provide a visual indicator system, wherein the microcontroller is further configured to visualize one or more non-scannable regions on the one or more light strips, corresponding to a seventh preconfigured finger gesture of visualizing the non-scannable regions.

Embodiments can provide a visual indicator system, wherein the visual indicator system further includes a pressure sensor or a weight sensor, configured to detect a human body on the medical imaging patient bed. The microcontroller is further configured to illuminate lights corresponding to the human body, such that a placement of the human body is visualized on the one or more light strips.

Embodiments can provide a visual indicator system, wherein the visual indicator system includes at least two light strips, each light strip corresponding to a predetermined medical imaging type. The microcontroller is further configured to illuminate the at least two light strips, and each light strip is configured to visualize a predetermined scan range for the predetermined medical imaging type.

Embodiments can provide a visual indicator system, wherein the microcontroller is further configured to enable a scan range planning mode by performing an eighth preconfigured finger gesture.

Embodiments can provide a medical imaging patient bed having an integrated visual indicator system, comprising: a medical imaging patient bed; one or more light strips, each light strip comprising a plurality of lights, the one or more light strips mounted to the medical imaging patient bed; a laser distance meter attached to one end of the medical imaging patient bed. The laser distance meter further comprising: a laser source configured to emit an emitted laser; and a laser receiver configured to receive a reflected laser; a storage device, configured to store one or more preconfigured finger gestures; a microcontroller; and a power source configured to provide power to the one or more light strips, the laser distance meter, the storage device, and the microcontroller. The microcontroller is configured to illuminate the one or more light strips after the one or more preconfigured finger gestures are made with respect to the one or more light strips. A position of illumination of the one or more light strips corresponds to a position of performing the one or more preconfigured finger gestures and one or more distance measurements received from the laser distance meter. The visual indicator system further comprises a reflective portion, attachable to the other end of the medical imaging patient bed and configured to reflect the emitted laser and produce the reflected laser.

Embodiments can provide a medical imaging patient bed wherein the microcontroller is further configured to illuminate at least two lights corresponding to a scan range selected through the one or more preconfigured finger gestures. An upper limit of the scan range corresponds to a first light and a lower limit of the scan range corresponds to a second light.

Embodiments can provide a medical imaging patient bed, further comprising a channel on a side of the medical imaging patient bed, the channel configured to accommodate the emitted laser and form a laser path.

Embodiments can provide a medical imaging patient bed, further comprising a finger guide on a sidewall of the channel, the finger guide configured to guide a finger to move along the laser path, wherein the one or more light strips are substantially aligned with the finger guide.

Embodiments can provide a medical imaging patient bed, wherein the finger guide is a slot.

Embodiments can provide a medical imaging patient bed, wherein the one or more light strips are raised out of the slot.

Embodiments can provide a method of using a visual indicator system, comprising: generating, by a laser distance meter, an emitted laser; performing, by a human finger, one or more preconfigured finger gestures; receiving, by the laser distance meter, a reflected laser caused by reflection of the emitted laser from the human finger; generating, by the laser distance meter, based upon properties of the emitted laser and the reflected laser, one or more distance measurements; communicating, to a microcontroller, the one or more distance measurements; and illuminating, by the microcontroller, one or more light strips in a manner corresponding to the one or more distance measurements received from the laser distance meter and the one or more preconfigured finger gestures.

Embodiments can provide a method of using a visual indicator system, further comprising: communicating, by the microcontroller, the one or more distance measurements to a host controller of a medical imaging system; and adjusting, by the host controller, one or more parameters of a medical imaging session based upon the one or more distance measurements.

Embodiments can provide a method of using a visual indicator system, further comprising: communicating, by the host controller, a status of the medical imaging session to the microcontroller; illuminating, by the microcontroller, the one or more light strips to visualize the status of the medical imaging session.

Embodiments can provide a method of using a visual indicator system, further comprising: illuminating, by the microcontroller, the one or more light strips to form one or more interactive visual animations.

Embodiments can provide a method of using a visual indicator system, further comprising: illuminating, by the microcontroller, the one or more light strips to form one or more interactive visual animations.

Additional features and advantages of the invention will be made apparent from the following detailed description of illustrative embodiments that proceeds with reference to the accompanying drawings.

BRIEF DESCRIPTION OF THE DRAWING FIGURES

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 5 illustrates commands corresponding to preconfigured finger gestures, in accordance with embodiments described herein;

FIGS. 16A and 16B illustrate a graphical representations of visualizing a planned scan range, in accordance with embodiments described herein;

Figure 18A:
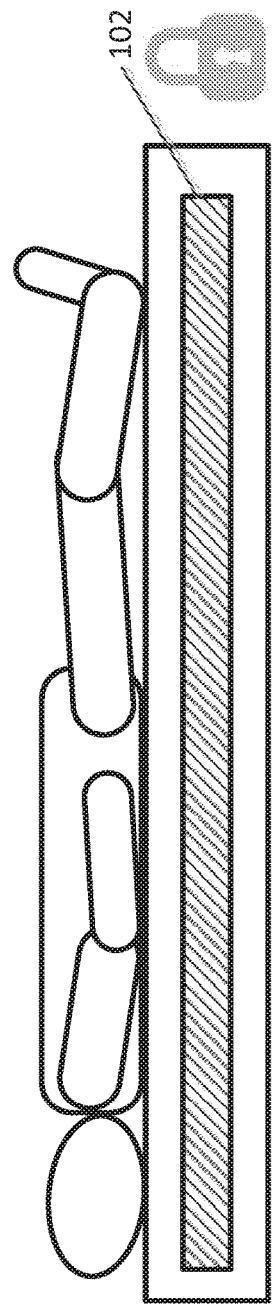
Figure 18B:
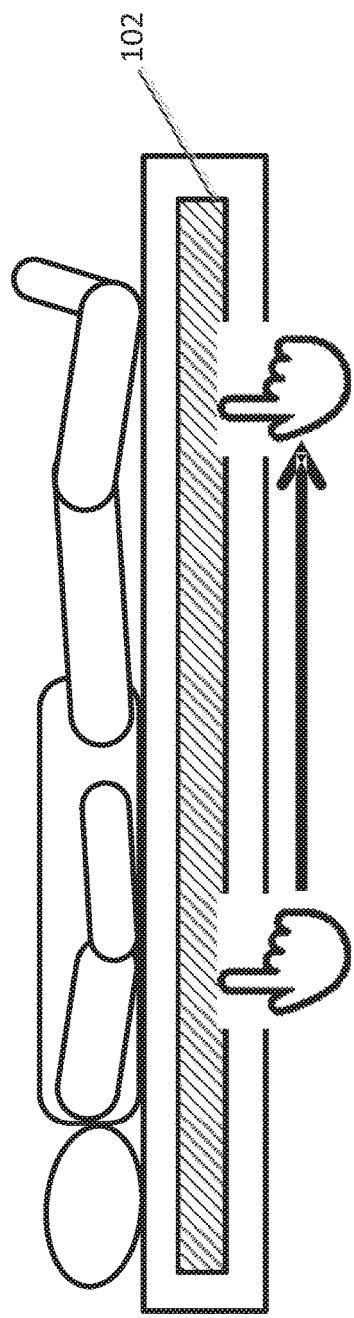
Figure 18C:
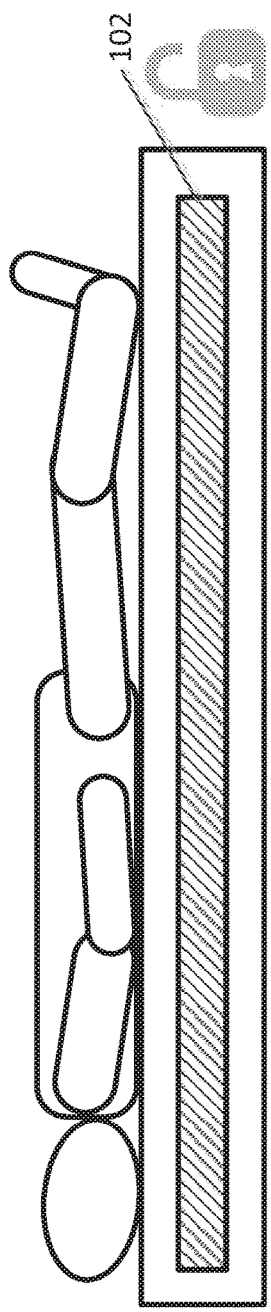
Figure 19:
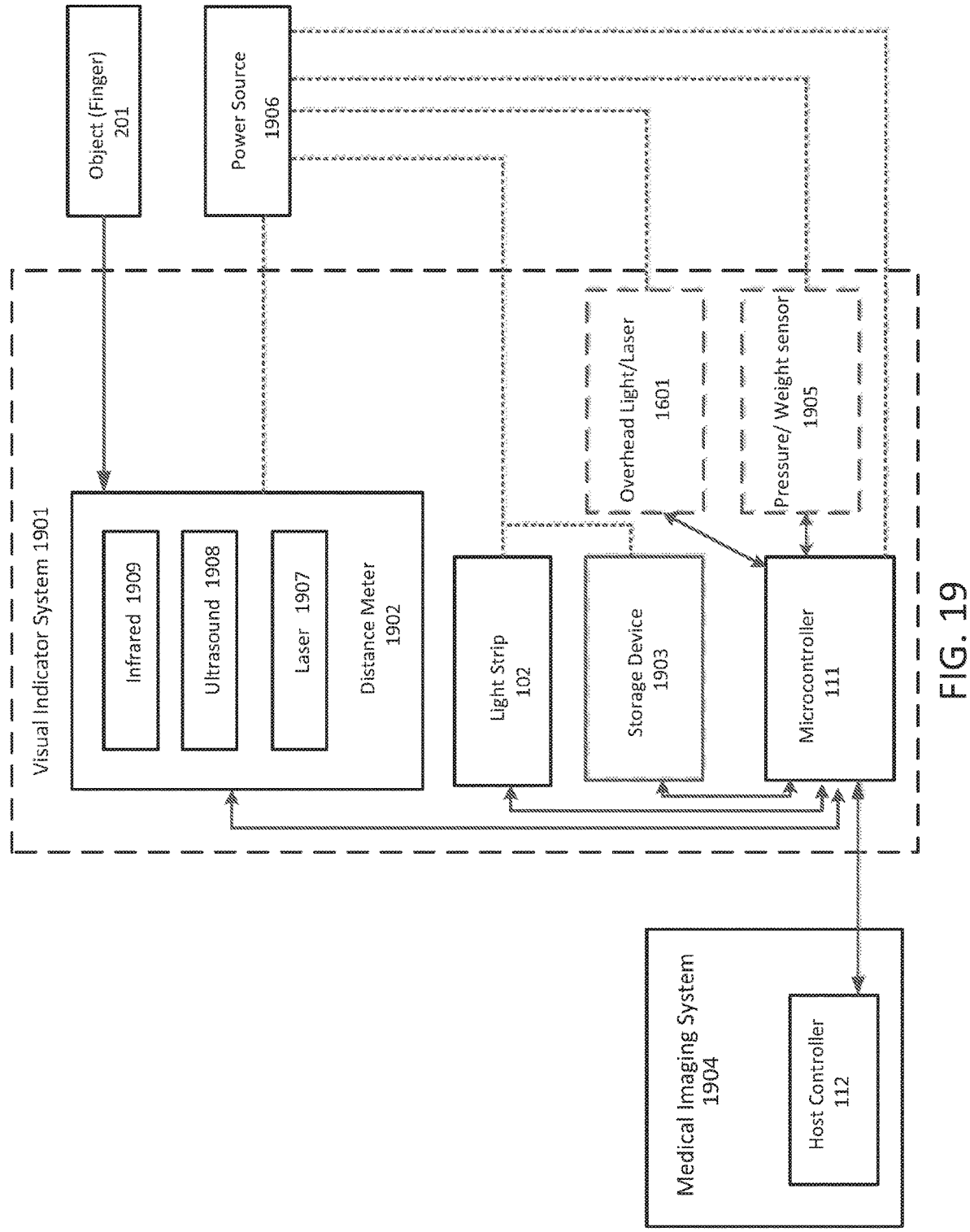

FIGS. 18A, 18B, and 18C illustrate graphical representations of unlocking the light strip, in accordance with embodiments described herein; and FIG. 19 illustrates a block diagram including various components of the visual indicator system, in accordance with embodiments described herein.

DETAILED DESCRIPTION

The following disclosure describes the present invention according to several embodiments directed to methods, systems, and apparatuses associated with a visual indicator system for a patient bed.

Embodiments of the present invention involve a system and method for providing bedside scan range planning during imaging and other medical sessions in a non-invasive manner, using a laser, ultrasound, or infrared rangefinder, one or more LEDs, a storage device, and a microcontroller connected to a host controller included in an imaging scanner. In embodiments, a visual indicator system may display a scan range graphically, or provide a digital output directly to the host controller of the imaging scanner.

Embodiments of the present invention further provide a system and method for providing status indication during imaging and other medical sessions, using one or more LEDs, a microcontroller, and an imaging scanner. In embodiments, the imaging scanner may provide a status of the medical imaging session to the microcontroller through the host controller, and the microcontroller may control the one or more LEDs to alert the clinic user to the status of the medical imaging session.

Embodiments of the present invention further provide a system and method for providing interactive aesthetic animations during imaging and other medical sessions, using one or more LEDs, and a microcontroller. The microcontroller may control the one or more LEDs to provide aesthetic animations, with which the clinic user or a patient may interact.

Figure 1:
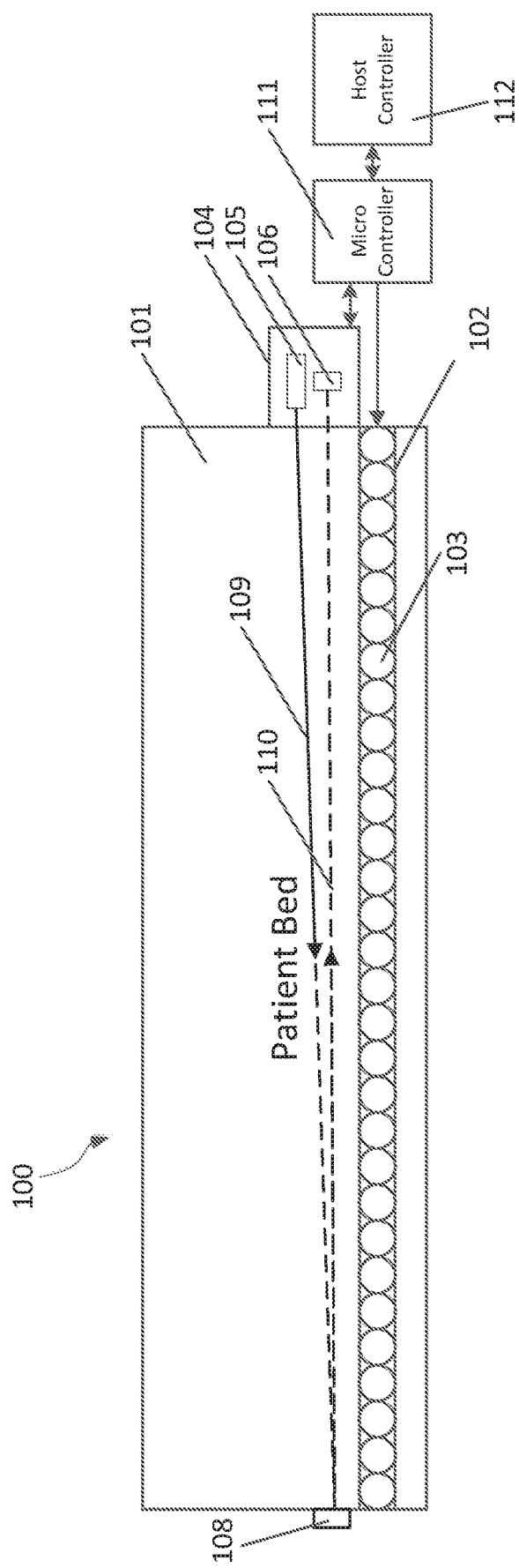
FIG. 1 illustrates a graphical representation of the visual indicator system, in accordance with embodiments described herein.

FIG. 1 illustrates a graphical representation of the visual indicator system 100, in accordance with some embodiments described herein. The visual indicator system 100 may be directly attached to a movable patient bed 101, or may be modular and detachable such that the system may be moved from bed to bed if needed. The visual indicator system 100 may have a light strip 102, which may include one or more lights 103. In an embodiment, the one or more lights 103 may be LEDs, but any high-efficiency lighting solutions may be employed. The one or more lights 103 may have the same or different colors, or may be color-changing LEDs. Alternatively, the light strip 102 may comprise a single, long screen comprising one or more pixels, which may function in a similar manner to the one or more lights 103. In an embodiment, the light strip 102 is positioned behind a wire mesh or other transparent protective panel. In an embodiment, the light strip 102 is mounted to the patient bed 101, or may be a separate unit attached to the patient bed 101. The resolution of the light strip 102 may vary based on the number of lights 103 incorporated into the light strip 102; for example, more lights 103 may be used in some embodiments to provide finer resolution.

To sense distances, the visual indicator system 100 may use a laser distance meter 104 comprising a laser source 105 and a laser receiver 106. The laser distance meter 104 may be configured to produce emitted laser beam 109 from the laser source 105, and the emitted laser beam 109 may travel within a channel 115 longitudinally located at one side of the patient bed 101 (see FIGS. 3 and 4).

In this example, the laser distance meter 104 is attached at one end of the channel 115, and a reflective portion 108 may be provided at the other end of the laser distance meter 104. The channel 115 may be V-shaped, arc-shaped, semi-circular, or of other shape. The channel 115 prevents interference of the emitted laser beam 109 from other objects or liquids in the clinic where the visual indicator system 100 may be located. The laser source 105 is located at one end of the channel 115, in which a laser path may be provided.

Figure 3:
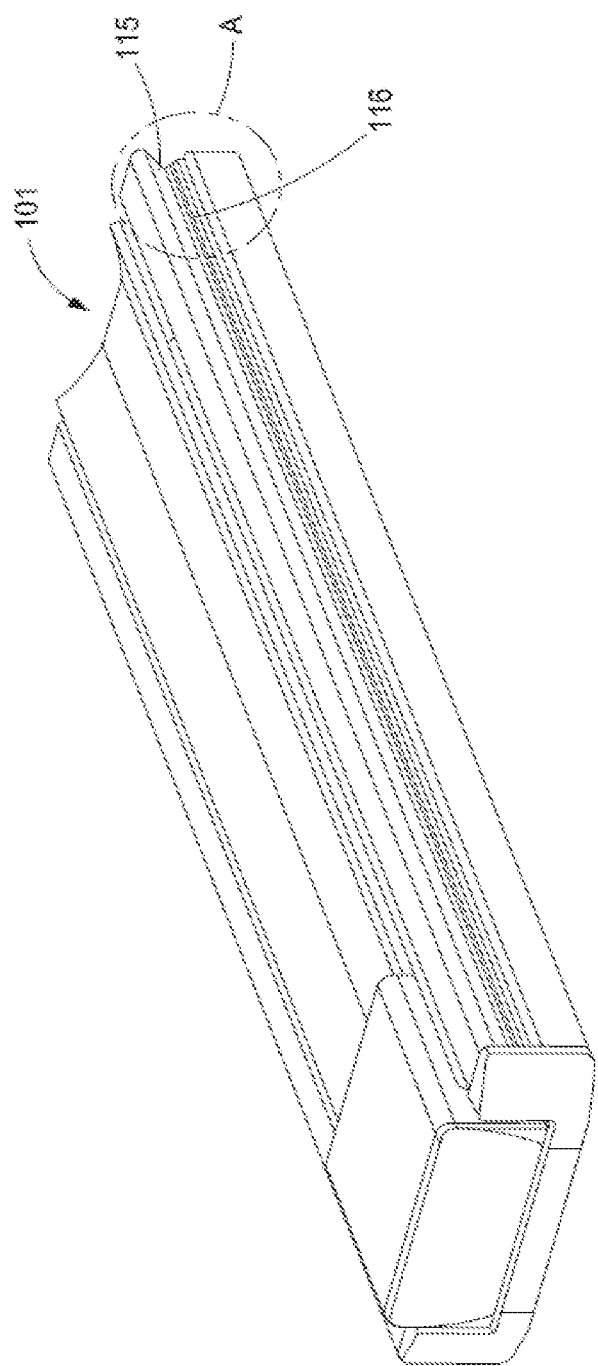
FIG. 3 illustrates a schematic diagram of a movable patient bed, in accordance with embodiments described herein.
Figure 4:
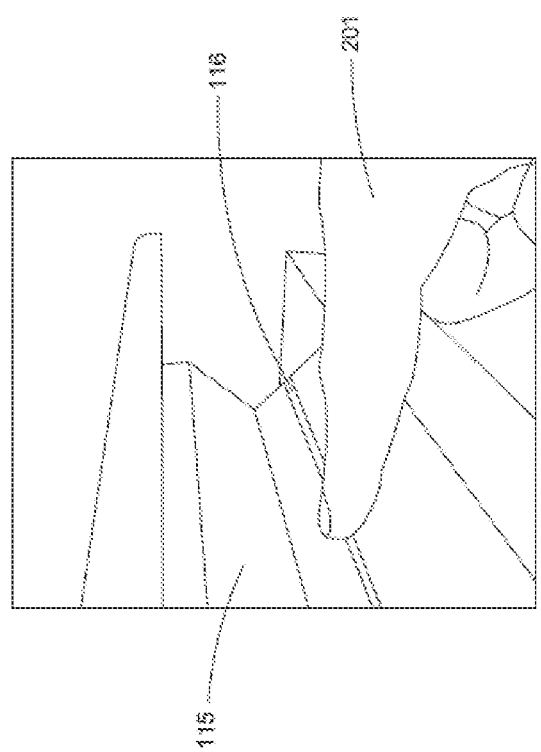
FIG. 4 illustrates an enlarged part A as shown in FIG. 3, in accordance with embodiments described herein.

FIG. 3 shows a schematic illustration of a movable patient bed 101, and FIG. 4 shows an enlarged part A as illustrated in FIG. 3. These figures illustrate a finger guide 116 provided on one sidewall of the channel 115. The finger guide 116 may be a slot and provided along the channel 115. As shown in FIG. 4, the finger guide 116 may be V-shaped; but, in general a guide of any shape capable of allowing movement of a human finger can be employed. The finger guide 116 provides a guide path for a finger (or other object, for example a stylus). Because the finger guide 116 is provided on one sidewall of the channel 115 through which the emitted laser beam 109 travels, the finger may move along the laser path or the finger may block the emitted laser beam 109 altogether. In some embodiments, the finger guide 116 and the channel 115 have the same length as the patient bed 101. In an embodiment, the light strip 102 is located behind the finger guide 116, so that the light is emitted by the light strip 102 through the finger guide 116. In an embodiment, the light strip 102 is slightly raised out of the finger guide 116. Thus, when the finger moves along the finger guide 116, the finger may touch the slightly raised light strip 102.

Returning to FIG. 1, at the other end of the channel 115 opposite the laser distance meter 104, a reflective portion 108 is located. The reflective portion 108 may be, for example, a mirror or other reflective surface, capable of reflecting the emitted laser beam 109 and producing reflected laser beam 110. The reflected laser beam 110 travels back along the channel 115 and is detected by the laser receiver 106. In some embodiments, the reflective portion 108 are used for calibration and resetting of the laser distance meter 104 after use by a clinic user.

Various types of laser sources may be used in accordance with different embodiments of the present invention. For example, in some embodiments, the laser source 105 is a visual laser source, such as a red laser. Alternatively, in other embodiment, an infrared laser or other low power laser may be used by the laser distance meter 104. In another alternative embodiment, an ultrasound distance meter or an infrared (but non-laser) distance meter is used in place of the laser distance meter 104. These embodiments may use an ultrasound source and ultrasound receiver or an infrared source and infrared receiver, respectively, to measure distances.

In the example of FIG. 1, the visual indicator system 100 controls the light strip 102 and the laser distance meter 104 through the use of a microcontroller 111. The microcontroller 111 interfaces with a host controller 112, which may be connected to a particular medical system, such as a medical imaging scanner (not shown in FIG. 1), via direct or indirect network connection. In this way, the microcontroller 111, in addition to visually displaying a scan range through the light strip 102, may also send a digital value of the scan range to the host controller 112 for display or recordation on the particular medical imaging scanner being used. The host controller 112 may adjust parameters of a medical imaging session, so that the medical imaging session may be performed with the scan range. Further, the medical imaging scanner may send the status data of the medical imaging session to the microcontroller 111 via the host controller 112, and the microcontroller 111 may control the light strip 102 to visualize the status of the medical imaging session so that the clinic user may be alerted.

Figure 2:
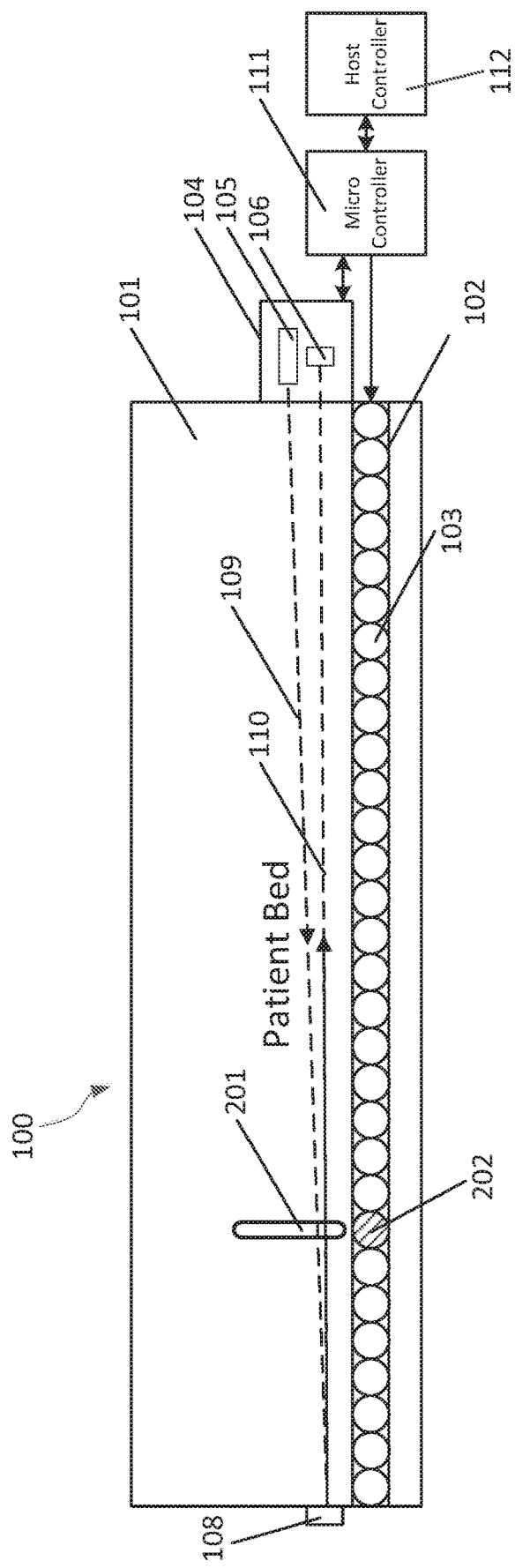
FIG. 2 illustrates a graphical representation of using the visual indicator system, in accordance with embodiments described herein.

FIG. 2 illustrates a graphical representation of using the visual indicator system 100 with a finger or other object 201 inserted in the figure guide 116 (see FIGS. 3 and 4), in accordance with some embodiments described herein. As described above, the laser distance meter 104 may continuously produce, through the laser source 105, an emitted laser beam 109. Without obstruction, the emitted laser beam 109 is transmitted along the channel 115, before being reflected from the reflective portion 108 opposite the laser source 105, and returned as a reflected laser beam 110 to the laser receiver 106. To use the visual indicator system 100 to make measurements and visually display a scan range, a clinic user may make a preconfigured gesture with a finger 201 on the finger guide 116 (see FIGS. 3 and 4) of the patient bed 101 at desired positions. The desired positions may correspond to, for example, an area just imaged, the location of a body part, or another metric determined to be important to the clinic user. It should be noted that, although this example refers to a finger 201 being inserted, in general any object can be inserted in the finger guide 116 and cause a similar response from the visual indicator system 100.

By putting the finger 201 on the finger guide 116 of the patient bed 101, the emitted laser beam 109 is truncated, and the reflected laser beam 110 returns with a different time than when unobstructed. This is also known as a time-of-flight calculation. The reflected laser beam 110 is received by the laser receiver 106 and used to determine a distance value indicative of the distance between the receiver and the finger 201. Then, this distance value may be communicated to the microcontroller 111. Based on the distance value sent to the microcontroller 111, the microcontroller 111 may send a command to the light strip 102 to activate one or more lights 103. For example, the light 202 may be illuminated such that it corresponds in position to the user's finger 201 on the finger guide 116 (See FIGS. 3 and 4).

Alternatively, the emitted laser beam 109 and reflected laser beam 110 may be used to determine distance through optical triangulation instead of time-of-flight. In optical triangulation, the distance of the finger 201 may be calculated through a measurement of the angular difference between the emitted laser beam 109 and the reflected laser beam 110, which may vary based upon the distance of the finger or other object 201 from the laser source 105 and the laser receiver 106.

In an embodiment, when a first limit of a scan range (e.g., an upper limit of the scan range) is selected by the finger 201 on the finger guide 116, a single light on the light strip 102 corresponding to the first limit may be illuminated. When a second limit of the scan range (e.g., a lower limit of the scan range) is selected by the finger 201 on the finger guide 116, then all the lights on the light strip 102 corresponding to the scan range between the first limit and the second limit may be illuminated. Alternatively, instead of illuminating all the lights, a pattern of lights on the light strip 102 may be used, where some are illuminated and some are extinguished. In other embodiments, only two lights may be illuminated on the light strip 102, corresponding to the first limit and the second limit, respectively. The lights on the light strip 102 may remain constantly illuminated, or may illuminate and extinguish in a periodic fashion. Alternatively, the lights may remain illuminated for a predetermined interval after the user's finger 201 is removed, or the lights may remain illuminated until a reset is communicated by the microcontroller 111 or until the finger 201 selects another scan range on the finger guide 116. The light strip 102 may completely extinguish when a reset command is sent by the microcontroller, or when the user makes a particular preconfigured finger gesture to clear the light strip 102.

In some embodiments, as the one or more lights 103 are illuminated, a digital value of the distance measured is communicated by the microcontroller 111 to a host controller 112 for storage, use, and/or display on a screen or monitor (not shown in the figures). In an embodiment, each time a user's finger 201 is put into the channel 115, a measurement communication may occur between the microcontroller 111 and the host controller 112 (as described above).

FIG. 5 illustrates commands corresponding to preconfigured finger gestures, in accordance with some embodiments described herein. With respect to the "swipe" finger gesture, if the clinic user swipes on the raised light strip 102 or on the finger guide 116, a scan range planning mode is enabled, allowing the clinic user to set the scan range for a medical imaging session. If the clinic user performs a "single tap" finger gesture at a certain position of the light strip 102, a position of the scan range is selected. For example, the user may use a "single tap" finger gesture to select a lower limit of the scan range and another "single tap" finger gesture to select an upper limit of the scan range. Then the lights between the two positions of the light strip 102 may be illuminated. Alternatively, the clinic user may select the upper limit of the scan range first, and then select the lower limit of the scan range.

Continuing with reference to FIG. 5, the clinic user may perform a "hold and drag" finger gesture to move the scan range by placing a figure at a position corresponding to any one of the illuminated lights and moving the figure to a new position. After completing the gesture, the lights corresponding to the new location of the scan range are illuminated and the lights corresponding to the old location of the scan range are extinguished.

The lights on the light strip 102 corresponding to the scan range may be extinguished when the clinic user performs a "double tap" finger gesture by tapping two times on the light strip 102 or on the finger guide 116 to reset the light strip 102. If there are several scan ranges selected by the clinic user, in an embodiment, the clinic user may double tap on a specific scan range to extinguish the lights corresponding to this scan range while the lights corresponding to other scan ranges may still be illuminated. Alternatively, the clinic user may double tap on any position of the light strip 102 or the finger guide 116 to reset and extinguish the lights corresponding to all the scan ranges. It should be appreciated that the commands and preconfigured finger gestures as showed in FIG. 3 are merely illustrative examples. The commands may correspond to different finger gestures. For example, the command "switch to scan range planning mode" may correspond to the gesture "spread." Further, FIG. 5 is intended to be non-limiting and is not exhaustive of all the possible commands and preconfigured finger gestures.

Figure 6:
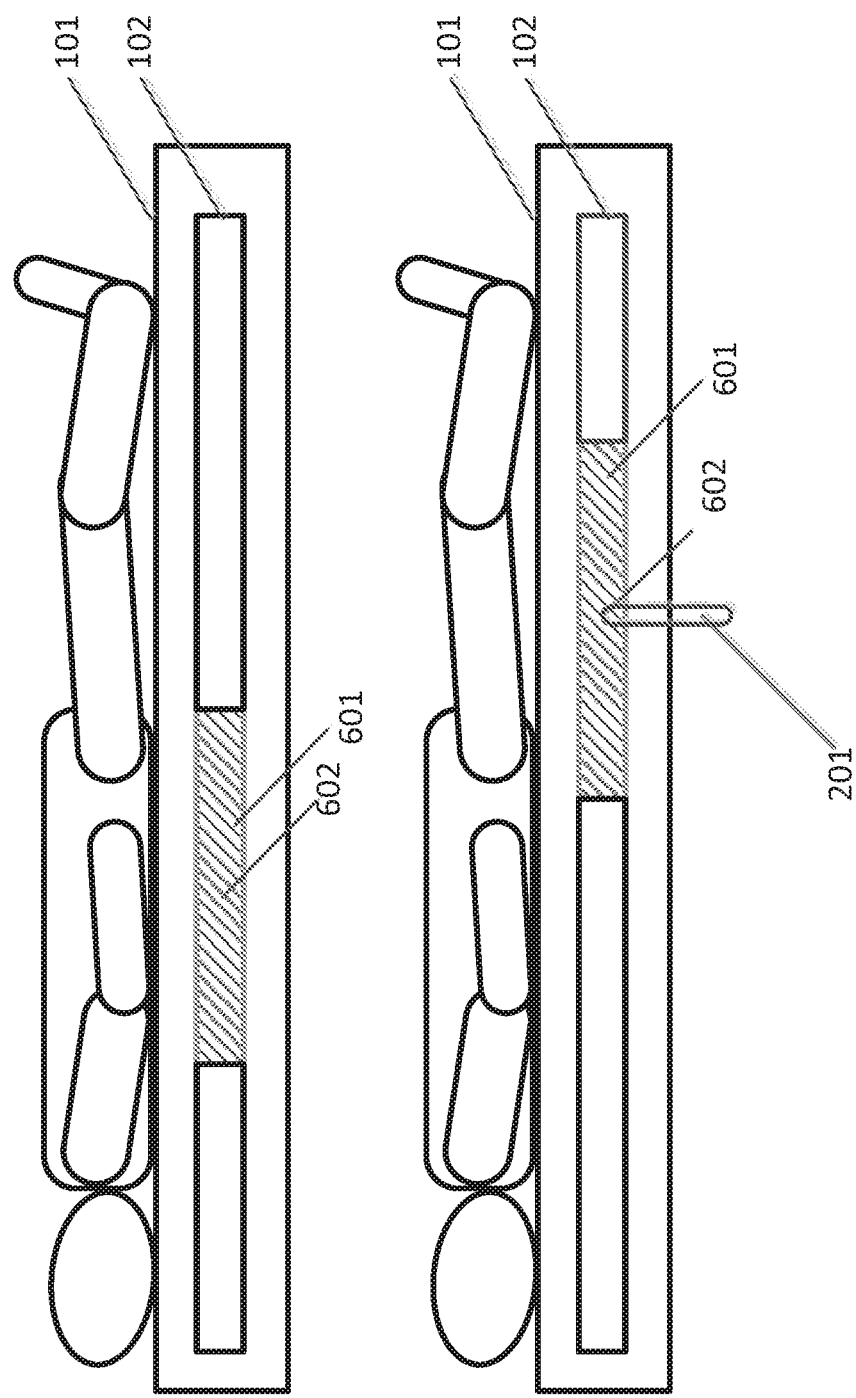
FIG. 6 illustrates a graphical representation of moving a scan range, in accordance with embodiments described herein.

FIG. 6 illustrates a graphical representation of moving a scan range, in accordance with some embodiments described herein. In this example, the lights of the light strip 102 corresponding to a scan range 601 are illuminated. The user may single tap the center 602 of the scan range 601, and then hold at the center 602 and drag the scan range 601. The scan range 601 may be moved to a new position on the light strip 102 selected by the user. The finger of the user may be kept at the center 602 during the movement. The embodiment of moving a scan range may be applicable to various types of scans including, for example, the whole-body CT scan, the whole-body planar scan and the whole-body single-photon emission computerized tomography (SPECT) scan.

Figure 7:
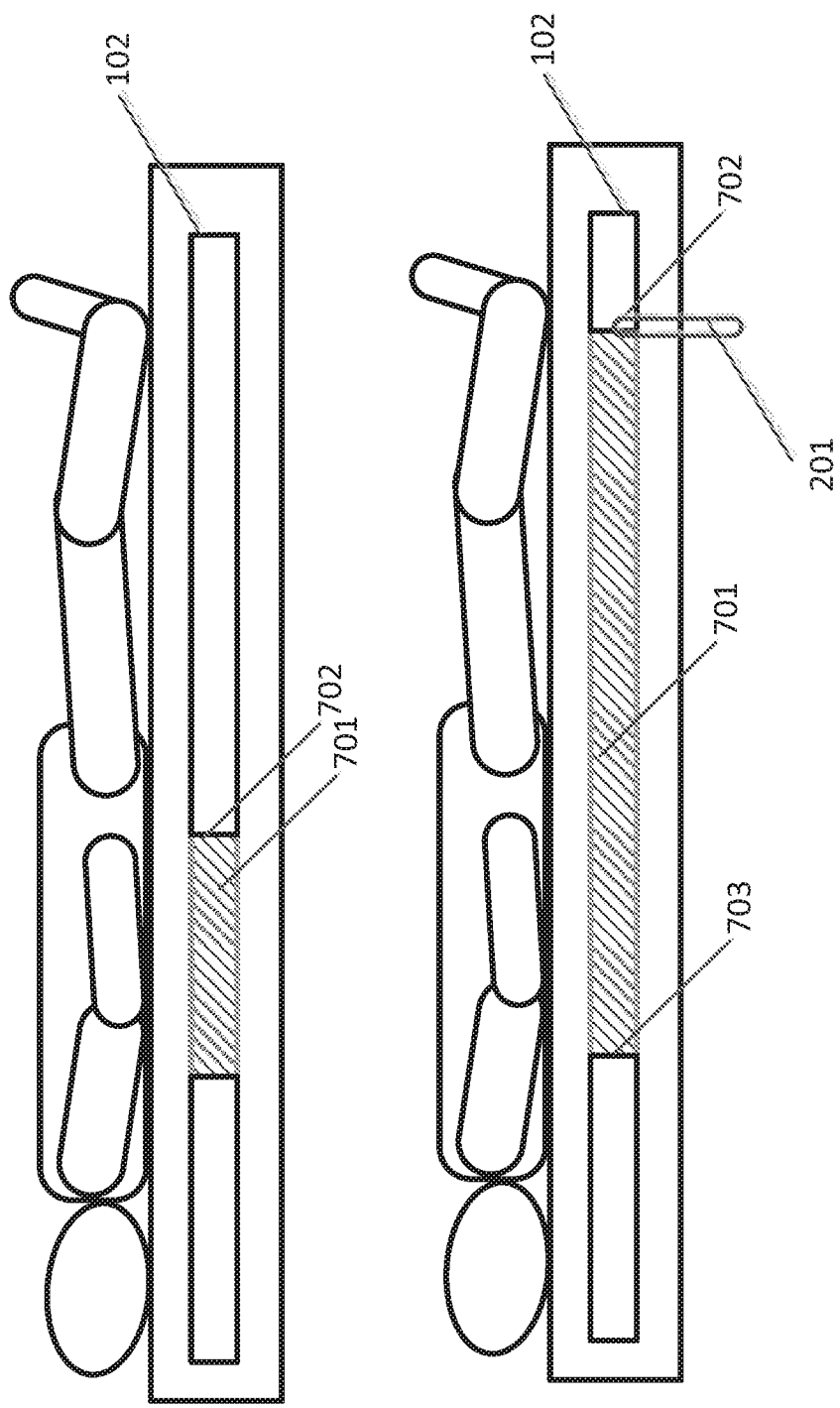
FIG. 7 illustrates a graphical representation of extending a scan range, in accordance with embodiments described herein.

FIG. 7 illustrates a graphical representation of extending a scan range, in accordance with some embodiments described herein. In this example, the lights of the light strip 102 corresponding to a scan range 701 are illuminated. The user may single tap to select the upper limit 702 of the scan range 701, and drag the upper limit 702. The upper limit 702 of the scan range 701 may be moved or extended to a new position on the light strip 102 designated by the clinic user, with the lower limit 703 remaining at the same position. The embodiment of extending a scan range may be applicable to various types of scans including, for example, the whole-body CT scan, the whole-body planar scan and the whole-body SPECT scan.

Figure 8:
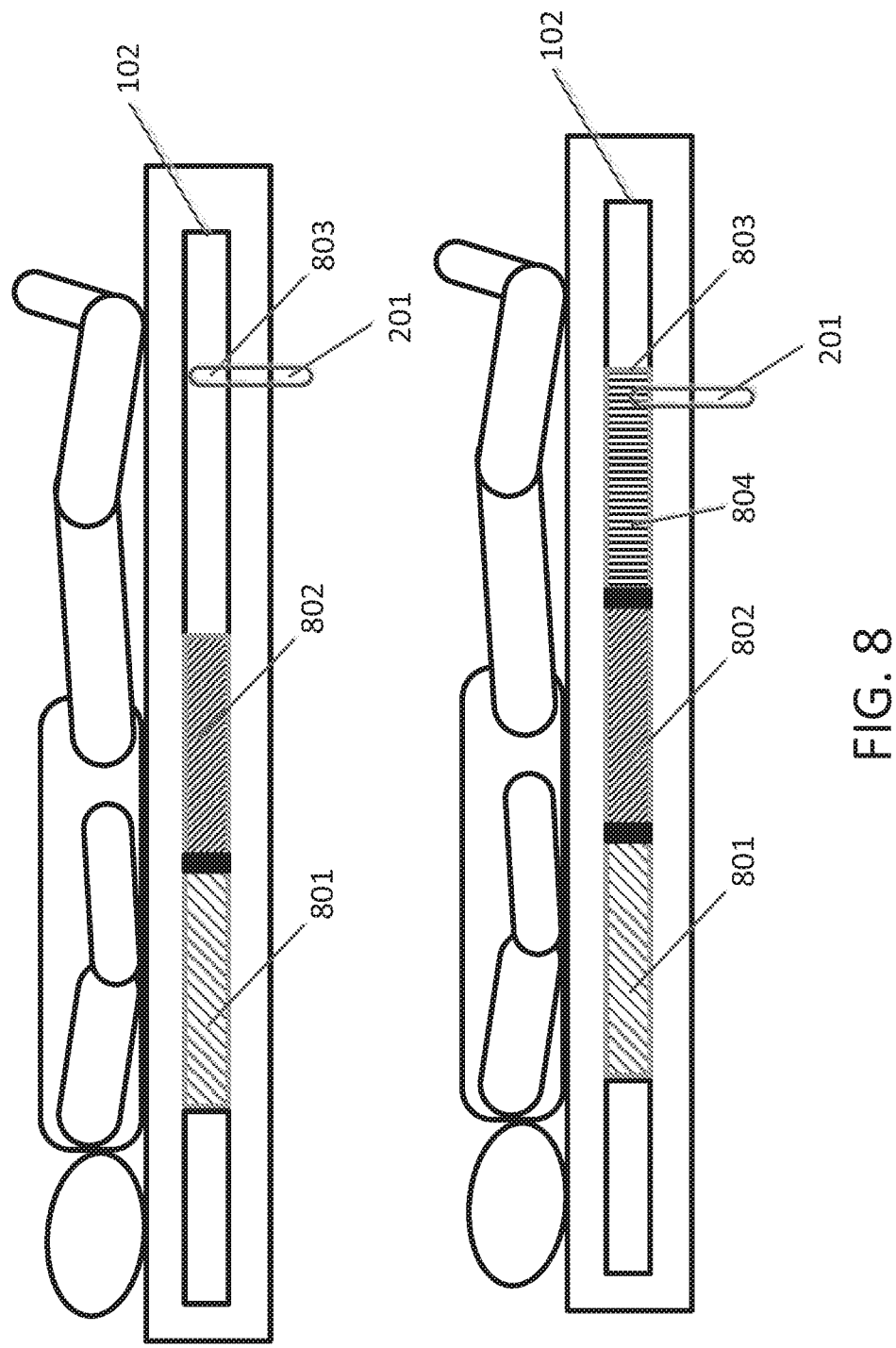
FIG. 8 illustrates a graphical representation of adding a scan range, in accordance with embodiments described herein.

FIG. 8 illustrates a graphical representation of adding a scan range, in accordance with some embodiments described herein. In an embodiment, the lights of the light strip 102 corresponding to a first scan range 801 and a second scan range 802 may be illuminated. The clinic user may single tap the light strip 102 to select an upper limit 803 for a new third scan range 804, perform a "pinch" gesture next to the upper limit 803, and then the new third scan range 804 may be added beside the second scan range 802 on the light strip 102. The embodiment of adding a scan range may be applicable to the whole-body SPECT scan.

Figure 9:
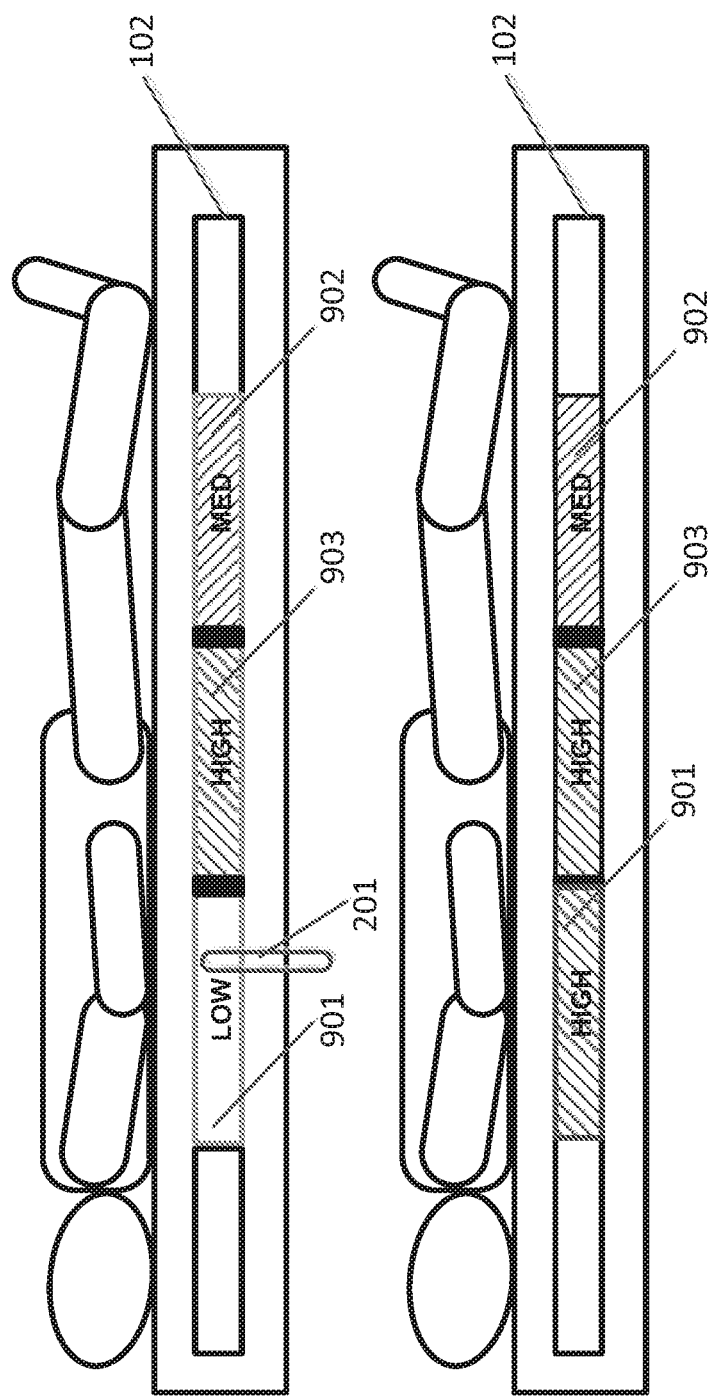
FIG. 9 illustrates a graphical representation of dynamically adjusting an image quality for each scan range with respect to human body anatomy, in accordance with embodiments described herein.

FIG. 9 illustrates a graphical representation of dynamically adjusting an image quality for each scan range with respect to human body anatomy, in accordance with some embodiments described herein. In this example, the lights of the light strip 102 corresponding to a first scan range 901, a second scan range 902 and a third scan range 903 are illuminated, and characteristics such as the brightness, saturation and/or color of these lights may be dynamically adjusted. In an embodiment, the image quality may be categorized as "Low," "Medium," and "High." For example, if the image quality of the first scan range 901 is low, the lights corresponding to the first scan range 901 may be illuminated with light red. If the image quality of the second scan range 902 is medium, the lights corresponding to the second scan range 902 may be illuminated with brick red. If the image quality of the third scan range 903 is high, the lights corresponding to the third scan range 903 may be illuminated with bright red. In an embodiment, the user may single tap any position of the first scan range 901 to select the first scan range 901. Then, the user may continue to single tap any position of the first scan range 901 to change the image quality. For example, the user may single tap any position of the first scan range 901, the image quality of the first scan range 901 may be changed from "Low" to "Medium." The user may single tap any position of the first scan range 901 again, the image quality of the first scan range 901 may be changed from "Medium" to "High." Similarly, the image quality of the second scan range 902 and the third scan range 903 may be changed in the same way. The embodiment of adjusting an image quality may be applicable to all the whole-body scans, for example, the whole-body CT scan, the whole-body planar scan, and the whole-body SPECT scan. It should be appreciated that the image quality may have more and different categories, for example, "class 1," "class 2," "class 3," "class 4," "class 5," "class 6", etc., with improved image quality. The example of FIG. 9 is intended to be non-limiting and is not exhaustive of all the possible image quality categories.

Figure 10:
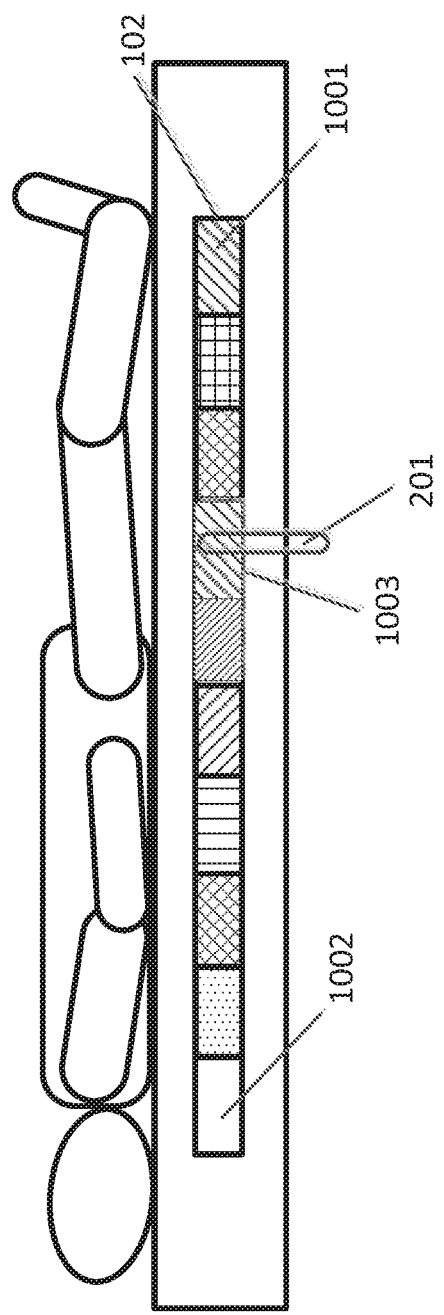
FIG. 10 illustrates a graphical representation of color spectrum with respect to a distance to the laser source, in accordance with embodiments described herein.

FIG. 10 illustrates a graphical representation of a spectrum of values with respect to a distance to the laser source 105 (see FIGS. 1 and 2), in accordance with some embodiments described herein. In this example, a color spectrum is employed and the different patterns shown in FIG. 10 are used to represent the different colors in the spectrum. In an embodiment, the color, brightness and/or saturation of the lights along the light strip 102 are dynamically adjusted. In FIG. 10, the color spectrum with respect to laser source 105 is visualized on the light strip 102. Specifically, a first section 1001 is the one most close to the laser source 105, and the lights corresponding to the first section 1001 have the deepest color. A second section 1002 is the one farthest from the laser source 105, and the lights corresponding to the second section 1002 have the lightest color. The user may customize any section of the light strip 102. In an embodiment, the user may single tap any position of a third section 1003 to select the third section 1003. Then the user may continue to single tap any position of the third section 1003 to change the color, brightness and/or saturation of the third section 1003. For example, the user may single tap any position of the third section 1003, the color of the third section 1003 may be changed from "color 1" to "color 2." The user may single tap any position of the third section 1003 again, the color of third section 1003 may be changed from "color 2" to "color 3." The user may continuously single tap the third section 1003 until the desired color is obtained.

Figure 11:
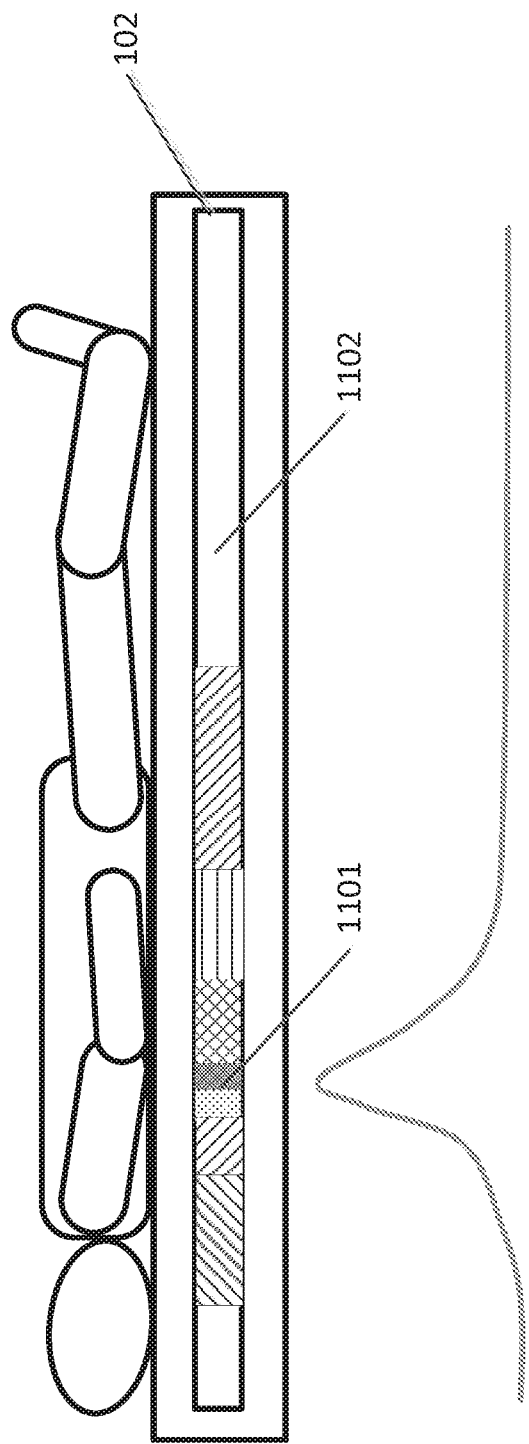
FIG. 11 illustrates a graphical representation of radioactive concentration of the latest acquisition with respect to the human body anatomy, in accordance with embodiments described herein.

FIG. 11 illustrates a graphical representation of radioactive concentration of the latest acquisition with respect to the human body anatomy, in accordance with some embodiments described herein. The different patterns shown in FIG. 11 are used to represent the radioactive concentration of the latest acquisition for the patient with regard to anatomical location. This information would not ordinarily be provided directly on the patient bed. However, using the visual indicator system shown in FIG. 11, the radioactive concentration is visualized through the light strip 102. In an embodiment, the visual indicator system may include a storage device (not shown in FIG. 11), which stores all the previous acquisition results. In another embodiment, the visual indicator system may access a remote server or cloud server, which stores all the previous acquisition results. The microcontroller 111 (shown in FIG. 1) may obtain the latest acquisition result or another previous acquisition result from the storage device, the remote server or cloud server, and then control the lights of the light strip 102 to visualize the radioactive concentration of the latest acquisition result or another previous acquisition result. In an embodiment, the radioactive concentration may be visualized with respect to the body anatomy of the patient. For example, if the chest of the patient was scanned with the highest radioactive concentration, then a section 1101 of the light strip 102 corresponding to the chest may be visualized with the deepest color. Conversely, a section 1102 of the light strip 102 corresponding to the lower legs of the patient may be visualized with the lightest color indicative of the lowest radioactive concentration. The radioactive concentration visualization of the previous acquisition result may facilitate the current scan range plan.

Figure 12:
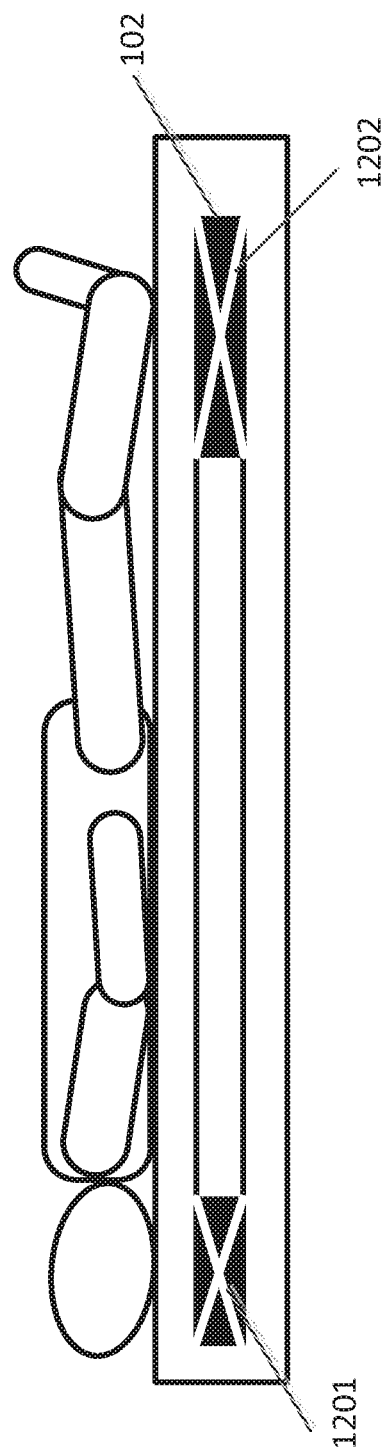
FIG. 12 illustrates a graphical representation of non-scannable regions, with respect to the human body anatomy, in accordance with embodiments described herein.

FIG. 12 illustrates a graphical representation of non-scannable regions, with respect to the human body anatomy, in accordance with some embodiments described herein. In this example, the non-scannable regions are the head and the lower legs of a patient; however, it should be understood that this concept can be applied to any non-scannable region. In FIG. 12, a section 1201 corresponding to the head and a section 1202 corresponding to the lower legs are displayed with a cross pattern. In another embodiment, the section 1201 and the section 1202 may be displayed with black color or in other patterns.

Figure 13:
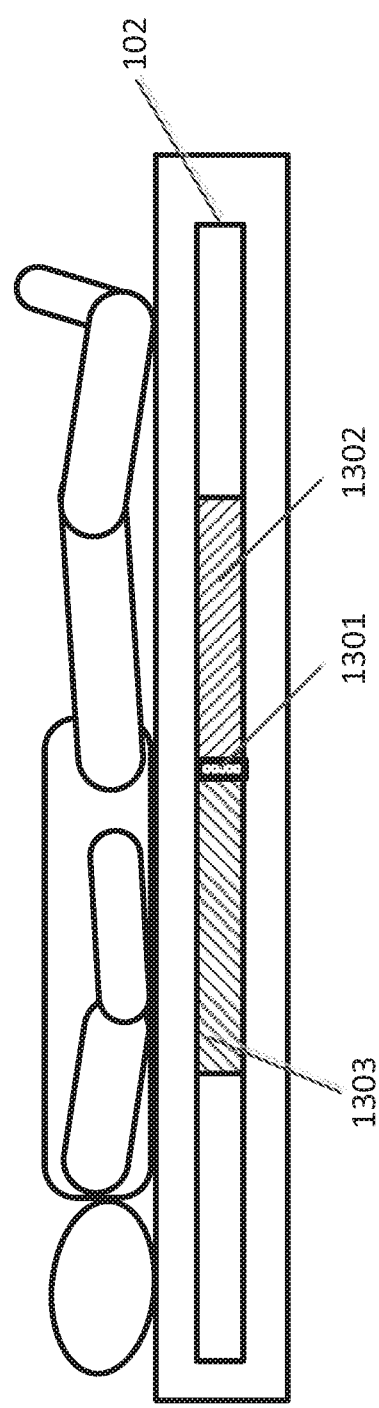
FIG. 13 illustrates a graphical representation of a boundary between two scan ranges, in accordance with embodiments described herein.

FIG. 13 illustrates a graphical representation of a boundary between two scan ranges, in accordance with some embodiments described herein. In this example, a boundary 1301 between two scan ranges 1302 and 1303 is visualized. This boundary 1301 may be useful, for example, when planning for a whole-body SPECT scan. In an embodiment, the lights corresponding to the boundary 1301 may be illuminated with a specific color (e.g., yellow). In another embodiment, the lights corresponding to the boundary 1301 may be illuminated with a specific pattern so that the user, for example a scan operator, may notice the boundary easily.

Figure 14:
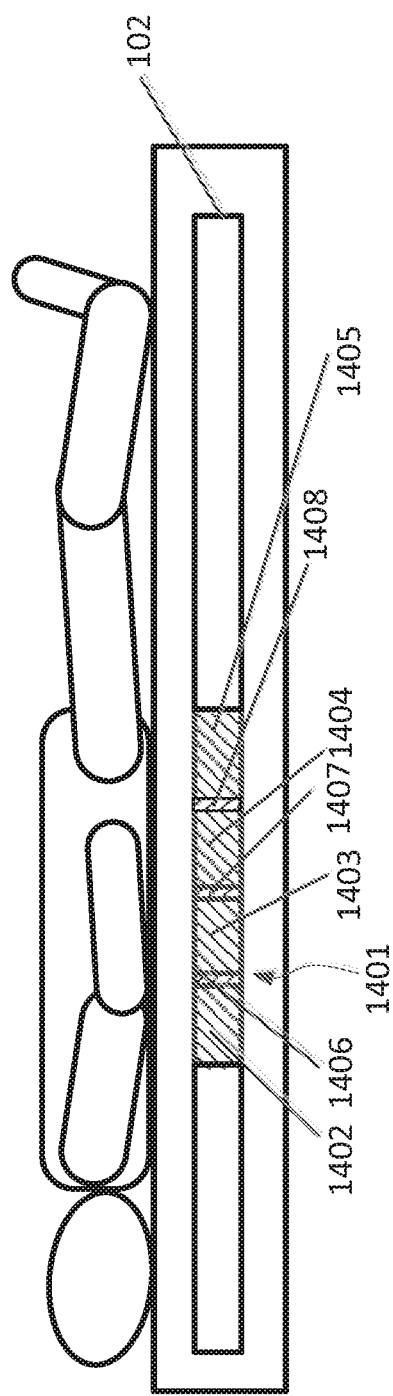
FIG. 14 illustrates a graphical representation of subdivided sections of a scan range, in accordance with embodiments described herein.

FIG. 14 illustrates a graphical representation of subdivided sections of a scan range, in accordance with some embodiments described herein. In this example, the scan range 1401 is divided into several sections, for example four quadrants 1402, 1403, 1404, and 1405, so that the relevant organs, for example the heart, and the lungs of the patient, may be centered or offset as necessary for a given clinical procedure. In an embodiment, the lights corresponding to boundaries 1406, 1407 and 1408 are illuminated with yellow color. In another embodiment, the lights corresponding to the boundaries 1406, 1407 and 1408 are illuminated with any color or any pattern so that the clinic user, for example, a scan operator, may notice the boundaries easily. In an embodiment, the four sections 1402, 1403, 1404, and 1405 can be moved or translated in a similar manner as illustrated in FIG. 6.

Figure 15:
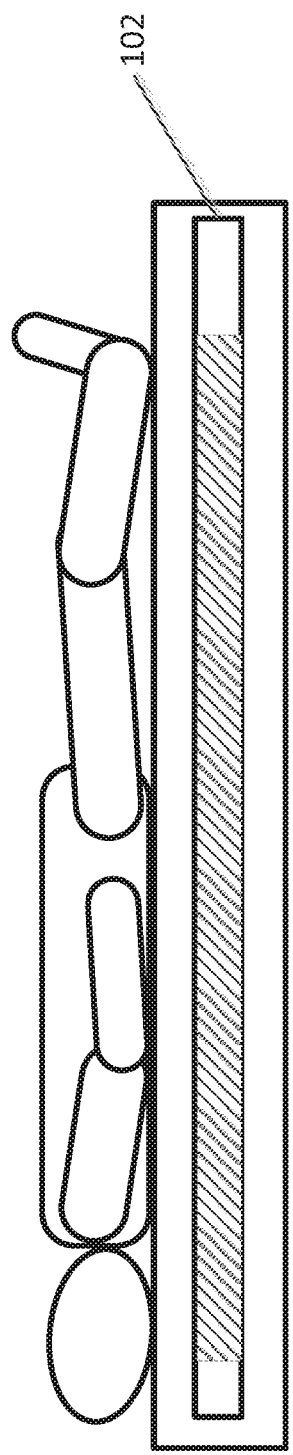
FIG. 15 illustrates a graphical representation of visualizing a body placement, in accordance with embodiments described herein.

FIG. 15 illustrates a graphical representation of visualizing a body placement, in accordance with some embodiments described herein. In this example, the visual indicator system may further include a sensor (e.g., a pressure sensor or a weight sensor), which is installed on the patient bed 101. When a patient lies on the patient bed 101, the sensor detects the patient body, and the microcontroller 111 may control the light strip 102 to visualize the body placement. In an embodiment, except non-scannable regions, the lights corresponding to the scannable part of the patient body may be visualized with a dark color. In another embodiment, the lights corresponding to the scannable part of the patient body may be visualized with any color or any pattern.

FIGS. 16A and 16B illustrate a graphical representation of visualizing a planned scan range, in accordance with some embodiments described herein. In these embodiments, the visual indicator system includes an overhead light or laser 1601. The overhead light or laser 1601 may be installed above a patient bed and substantially aligned with the center of the patient bed. When a scan range is set and visualized on the light strip 102, the microcontroller 111 may control the overhead light or laser 1601 to illuminate the corresponding part of the patient body, and the illuminated part may correspond to the set scan range (as shown in FIG. 16A). In an embodiment, when the clinic user, for example a scan operator, tries to move or translate the scan range in a way as illustrated in FIG. 6, the microcontroller 111 may control the overhead light or laser 1601 to illuminate the part of the patient body corresponding to the new scan range (as shown in FIG. 16B).

Figure 17:
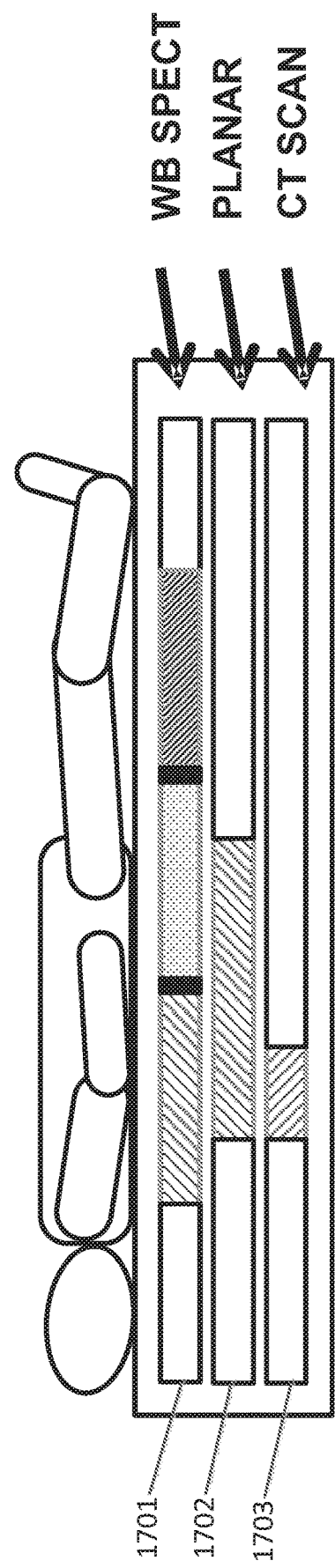
FIG. 17 illustrates a graphical representation of visualizing scan ranges of different scan types, in accordance with embodiments described herein.

FIG. 17 illustrates a graphical representation of visualizing scan ranges of different scan types, in accordance with embodiments described herein. In these embodiments, the user plans scan ranges for the entire workflow of a plurality of scans. In the example of FIG. 17, these scans include a whole-body CT scan, a whole-body SPECT scan and a whole-body planar scan; however, it should be understood that various types of scans may be used in combination. In an embodiment, light strip 102 includes a screen, the scan ranges of the different scan types are visualized on different rows of the screen respectively. For example, the planned scan range for the whole-body SPECT scan is shown on the first row, the planned scan range for the whole-body planar scan is shown on the second row, and the planned scan range for the whole-body CT scan is shown on the third row. Each scan range is visualized in different colors or patterns. In another embodiment, the visual indicator system may have more than one light strip, for example three light strips, each for a particular scan type. For example, as shown in FIG. 17, first light strip 1701 is provided for the whole-body SPECT scan, a second light strip 1702 is provided for the whole-body planar scan, and a third light strip 1703 is provided for the whole-body CT scan. The scan ranges on the first light strip 1701, the second light strip 1702, and the third light strip 1703 are visualized with different colors or patterns.

FIGS. 18A, 18B, and 18C illustrate a graphical representation of unlocking the light strip 102, in accordance with embodiments described herein. In FIG. 18A, the light strip 102 is in a locked mode. In FIGS. 18A and 18C, a graphical lock is shown for illustration purposes. In some embodiments, this lock, or a similar graphic, may be provided on the light strip 102 or a display of the moveable patient bed 101. While in lock mode, no finger gesture can trigger any operation on the light strip 102. In FIG. 18B, the user swipes on the light strip 102 to unlock the light strip 102, and enables the scan range planning mode. Finally, in FIG. 18C, the light strip 102 is unlocked and the user may then perform one or more preconfigured finger gestures to set and plan the scan range.

In an embodiment, the light strip 102 may also work as a status indicator to inform the clinic user, for example a scan operator, of the status of the imaging session. In an embodiment, when axes motion of the imaging system has been initiated and any axis may accelerate to motion at any time, the light strip 102 may be illuminated with red color, a different color or a combination of several colors to alert the clinic user to the automated motion state of the imaging system, so that the clinic user may avoid contact with the medical imaging system or machine. Moreover, after the scan range is set and the imaging session is ready, the clinic user may leave the imaging room where the scan session is performed, and thus the status of the scan session may be unnoticeable to him/her. In an embodiment, during the progress of the imaging session, the light strip 102 may be illuminated with yellow color, a different color or a combination of several colors. Alternatively, the lights of the light strip 102 may flash or change color in a periodic manner. In an embodiment, if the imaging session or an acquisition is completed, the light strip 102 may be illuminated with green color, a different color or a combination of several colors, and flashed in a periodic manner. In an embodiment, if the scan session is temporarily paused due to an error condition, the light strip 102 may be illuminated with red color, or flashed, so that the clinic user may notice the error condition and resolve the problem immediately.

In an embodiment, diverse animations may be provided through the lights of the light strip 102 to relieve the patient's anxiety. In an embodiment, the lights of the light strip 102 may be controlled by the microcontroller 111 to provide color-changing aesthetic appearance. Alternatively, the lights of the light strip 102 may provide a combination of various colors by moving and overlapping sinusoidal waves of various colors. In an embodiment, the lights of the light strip 102 may provide a color spectrum. The clinic user or the patient may select and change any color of the color spectrum through the preconfigured finger gestures. In an embodiment, the lights of the light strip 102 may provide a brightness spectrum. The clinic user or the patient may select and change any brightness of the brightness spectrum through the preconfigured finger gestures. In an embodiment, the lights of the light strip 102 may provide a saturation spectrum. The clinic user or the patient may select and change any saturation of the saturation spectrum through the preconfigured finger gestures.

In an embodiment, the lights of the light strip 102 provide "moving water" animations. The clinic user or the patient can interact with the "moving water" animations. When the finger of the clinic user or the patient is detected, for example, when the finger blocks the laser path, the "moving water" may ripple with different colors.

In an embodiment, the lights of the light strip 102 provide a stack animation. Specifically, blocks having an equal length or different lengths run down the strip, one at a time and stack on top of each other. In an embodiment, the lights of the light strip 102 provide a bounce animation, wherein a pixel may be shot from one end of the light strip 102 to the other end of the light strip 10 while being pulled down by gravity. The ball continues to bounce to lower heights until it comes to a rest, then the ball is shot up again. In an embodiment, the lights of the light strip 102 provide a droplet animation, wherein small rings expand from random locations along the light strip 102 and fade out, emulating the rings seen from raindrops.

In an embodiment, the lights of the light strip 102 provide a 2D object cut into several layers. The several layers are shown on the light strip 102 in a sequential order, as if a screen were scrolled past the 2D object. In an embodiment, the lights of the light strip 102 provide a twinkle animation, wherein a random glare may appear on a lit background, simulating glistens of stars or oceans. In an embodiment, the lights of the light strip 102 provide a sliding block animation, wherein blocks having an equal length or different lengths slide into the previous slot, one at a time. The color of each block changes with various color shades. In an embodiment, the lights of the light strip 102 provide a sunset or sunrise animation, wherein a series of color gradients radiating from the middle of the strip to look like a sunset or sunrise.

FIG. 19 depicts a block diagram illustrating various components of the visual indicator system 1901, in accordance with some embodiments described herein. As discussed above, the visual indicator system 1901 may be controlled via a microcontroller 111, which may mediate the interactions between a distance meter 1902 and a light strip 102. As the object (i.e., the user's finger) 201 interacts with the distance meter 1902 at one end of the patient bed 101, the microcontroller 111 may turn lights in the light strip 102 on and off with respect to the preconfigured finger gestures and the measured distances. The preconfigured finger gestures may be stored in a storage device 1903. The storage device 1903 may further store previous acquisition results of all the patients. If one or more lights are illuminated (for instance, when visually displaying a scan range), the system may completely return to a basic operating state through the use of a reset command, which may be sent via a switch, button, toggle, or software command. Alternatively, the reset command may be provided by double tapping the light strip 102. The basic operating state may include extinguishing the light strip 102 and resetting the distance meter 1902. Additionally, the measured distances may be output by the microcontroller 111 to the host controller 112, which, in turn, may communicate with a medical imaging system 1904. Furthermore, the medical imaging system 1904 may communicate the status data of a medical imaging session to the microcontroller 111 via the host controller 112. The microcontroller 111 may control the light strip 102 to visualize the status of the medical imaging session for the clinic user. The microcontroller 111 may further control the light strip 102 to provide diverse interactive animations which may relieve the anxiety of patients. The visual indicator system 1901 may further include an overhead light or laser 1601, which may illuminate the body part corresponding to the set scan range. The visual indicator system 1901 may further include a pressure sensor or a weight sensor 1905, which may detect the patient body for body placement. The visual indicator system 1901 may be powered by a power source 1906, which may be an external plug or a battery. A battery may be used for portability, such that a patient bed 101 with the visual indicator system 1901 installed may be moved between rooms or within a large room without the need to unplug from and re-plug into the outlet.

Modes of measurement by the distance meter 1902 may include a laser distance meter 1907, an ultrasound distance meter 1908, or an infrared distance meter 1909. In an embodiment, the laser distance meter 1907, ultrasound distance meter 1908, or infrared distance meter 1909 determines distances through time-of-flight. Alternatively, the laser distance meter 1902 may determine distance through optical triangulation.

Advantages of embodiments of the visual indicator system include easy adjustment and planning of scan ranges through preprogrammed gesture commands, timely alert of the clinic user to the status of a medical imaging session, interaction with relaxing aesthetic animations, and flexibility of user input control.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one may also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes may be implemented using hardware components, software components, and/or combinations thereof. No claim element herein is to be construed under the provisions of 35 U.S.C. 112(f) unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A visual indicator system, attachable to a medical imaging patient bed, the visual indicator system comprising:
   a finger guide comprising a recessed channel along one side of the medical imaging patient bed;
   one or more light strips disposed within the finger guide, each light strip comprising a plurality of lights;
   a distance meter, attachable to one end of the medical imaging patient bed and configured to emit a laser beam along the finger guide;
   a storage device, configured to store one or more preconfigured finger gestures comprising gestures that include tapping a finger within the finger guide and moving a finger within the finger guide or a combination thereof; and
   a microcontroller;
   wherein the microcontroller is configured to detect when a finger truncates the beam in the finger guide, determine the location of the finger within the finger guide using the distance meter, and illuminate the one or more light strips after the one or more preconfigured finger gestures comprising are made with respect to the one or more light strips;
   wherein a position of the illumination of the light strip corresponds to a position of performing the one or more preconfigured finger gestures.

2. The visual indicator system as recited in claim 1, wherein the microcontroller is further configured to illuminate at least two lights corresponding to a scan range selected through the one or more preconfigured finger gestures,
   wherein an upper limit of the scan range corresponds to a first light and a lower limit of the scan range corresponds to a second light.

3. The visual indicator system as recited in claim 2, wherein the microcontroller is further configured to illuminate at least two lights different than previously illuminated lights, corresponding to a first preconfigured finger gesture of moving the scan range,
   wherein the upper limit of the scan range corresponds to a third light and the lower limit of the scan range corresponds to a fourth light.

4. The visual indicator system as recited in claim 2, wherein the microcontroller is further configured to illuminate at least two lights different than previously illuminated lights, corresponding to a second preconfigured finger gesture of extending the scan range,
   wherein the upper limit of the scan range corresponds to a third light while the lower limit of the scan range corresponds to the second light, or the upper limit of the scan range corresponds to the first light while the lower limit of the scan range corresponds to a fourth light.

5. The visual indicator system as recited in claim 2, wherein the microcontroller is further configured to illuminate additional lights, corresponding to a third preconfigured finger gesture of adding a new scan range,
   wherein the additional lights correspond to an upper limit of the new scan range and a lower limit of the new scan range.

6. The visual indicator system as recited in claim 2, wherein the microcontroller is further configured to change one or more of color, saturation, and brightness of the at least two lights, corresponding to a fourth preconfigured finger gesture of adjusting an image quality.

7. The visual indicator system as recited in claim 2, wherein the microcontroller is further configured to divide the scan range into a plurality of sections, and visualize the plurality of sections on the one or more light strips, corresponding to a fifth preconfigured finger gesture of dividing the scan range, wherein the microcontroller is further configured to visualize a boundary between every two sections on the one or more light strips.

8. The visual indicator system as recited in claim 2, wherein the visual indicator system further includes an overhead laser or an overhead light mounted above the medical imaging patient bed,
wherein the microcontroller is further configured to control the overhead laser or the overhead light to illuminate a part of a human body on the medical imaging patient bed, corresponding to the scan range.

9. The visual indicator system as recited in claim 2, wherein the microcontroller is further configured to illuminate the one or more light strips when a status of the medical imaging system changes.

10. The visual indicator system as recited in claim 9, wherein the microcontroller is further configured to illuminate the one or more light strips to form one or more interactive visual animations.

11. The visual indicator system as recited in claim 2, wherein the microcontroller is further configured to illuminate the one or more light strips to form one or more interactive visual animations.

12. The visual indicator system as recited in claim 1, wherein the distance meter comprises at least one of a laser distance meter, an ultrasound distance meter, or an infrared distance meter.

13. The visual indicator system as recited in claim 12, wherein the laser distance meter further comprises:
a laser source configured to emit an emitted laser; and
a laser receiver configured to receive a reflected laser;
wherein the visual indicator system further comprises a reflective portion, attachable to the other end of the medical imaging patient bed and configured to reflect the emitted laser and produce the reflected laser.

14. The visual indicator system as recited in claim 1, wherein the storage device further includes one or more previous acquisition results, and
wherein the microcontroller is further configured to visualize radioactive concentration of the one or more previous acquisition results on the one or more light strips, corresponding to a sixth preconfigured finger gesture of visualizing the radioactive concentration.

15. The visual indicator system as recited in claim 1, wherein the microcontroller is further configured to visualize one or more non-scannable regions on the one or more light strips, corresponding to a seventh preconfigured finger gesture of visualizing the non-scannable regions.

16. The visual indicator system as recited in claim 1, wherein the visual indicator system further includes a pressure sensor or a weight sensor, configured to detect a human body on the medical imaging patient bed,
wherein the microcontroller is further configured to illuminate lights corresponding to the human body, such that a placement of the human body is visualized on the one or more light strips.

17. The visual indicator system as recited in claim 1, wherein the visual indicator system includes at least two light strips, each light strip corresponding to a predetermined medical imaging type,
wherein the microcontroller is further configured to illuminate the at least two light strips, and each light strip is configured to visualize a predetermined scan range for the predetermined medical imaging type.

18. The visual indicator system as recited in claim 1, wherein the microcontroller is further configured to enable a scan range planning mode by performing an eighth preconfigured finger gesture.

19. A medical imaging patient bed having an integrated visual indicator system, comprising:
a medical imaging patient bed;
a finger guide comprising a recessed channel along one side of the medical imaging patient bed;
one or more light strips, each light strip comprising a plurality of lights, the one or more light strips mounted to the medical imaging patient bed;
a laser distance meter configured to emit a laser beam along the finger guide, the laser distance meter further comprising:
a laser source configured to emit an emitted laser; and
a laser receiver configured to receive a reflected laser;
a storage device, configured to store one or more preconfigured finger gestures;
a microcontroller; and
a power source configured to provide power to the one or more light strips, the laser distance meter, the storage device, and the microcontroller;
wherein the microcontroller is configured to detect when a finger truncates the beam in the finger guide, determine the location of the finger within the finger guide using the distance meter, and illuminate the one or more light strips after the one or more preconfigured finger gestures comprising gestures that include tapping a finger within the finger guide and moving a finger within the finger guide or a combination thereof are made with respect to the one or more light strips;
wherein a position of illumination of the one or more light strips corresponds to a position of performing the one or more preconfigured finger gestures and one or more distance measurements received from the laser distance meter;
wherein the visual indicator system further comprises a reflective portion, attachable to the other end of the medical imaging patient bed and configured to reflect the emitted laser and produce the reflected laser.

20. The medical imaging patient bed as recited in claim 19, wherein the microcontroller is further configured to illuminate at least two lights corresponding to a scan range selected through the one or more preconfigured finger gestures,
wherein an upper limit of the scan range corresponds to a first light and a lower limit of the scan range corresponds to a second light.

21. The medical imaging patient bed as recited in claim 19, further comprising a channel on a side of the medical imaging patient bed, the channel configured to accommodate the emitted laser and form a laser path.

22. The medical imaging patient bed as recited in claim 21, further comprising a finger guide on a sidewall of the channel, the finger guide configured to guide a finger to move along the laser path, wherein the one or more light strips are substantially aligned with the finger guide.

23. The medical imaging patient bed as recited in claim 22, wherein the finger guide is a slot.

24. The medical imaging patient bed as recited in claim 23, wherein the one or more light strips are raised out of the slot.

25. A method of using a visual indicator system, comprising:

generating, by a laser distance meter, an emitted laser in a finger groove placed along the side of an imaging patient bed;

performing, by a human finger, one or more preconfigured finger gestures in the finger groove, the gestures including at least tapping the human finger within the finger groove and moving the finger along the finger groove or any combination thereof;

receiving, by the laser distance meter, a reflected laser caused by reflection of the emitted laser from the human finger;

generating, by the laser distance meter, based upon properties of the emitted laser and the reflected laser, one or more distance measurements each time the finger reflects the emitted laser;

communicating, to a microcontroller, the one or more distance measurements; and determining, by the microcontroller, the one or more preconfigured finger gestures;

illuminating, by the microcontroller, one or more light strips in a manner corresponding to the one or more distance measurements received from the laser distance meter and the one or more preconfigured finger gestures.

26. The method as recited in claim 25, further comprising:

communicating, by the microcontroller, the one or more distance measurements to a host controller of a medical imaging system; and adjusting, by the host controller, one or more parameters of a medical imaging session based upon the one or more distance measurements.

27. The method as recited in claim 26, further comprising:

communicating, by the host controller, a status of the medical imaging session to the microcontroller;

illuminating, by the microcontroller, the one or more light strips to visualize the status of the medical imaging session.

28. The method as recited in claim 27, further comprising:

illuminating, by the microcontroller, the one or more light strips to form one or more interactive visual animations.

29. The method as recited in claim 25, further comprising:

illuminating, by the microcontroller, the one or more light strips to form one or more visual animations.

* * * * *